(12) United States Patent
Freudenberg et al.

(10) Patent No.: US 9,283,527 B2
(45) Date of Patent: Mar. 15, 2016

(54) SYSTEM FOR HANDLING DISPLACEMENT OF LIQUID PRODUCTS

(71) Applicant: Ecolab USA Inc., St. Paul, MN (US)

(72) Inventors: Jared R. Freudenberg, St. Louis Park, MN (US); Troy A. Anderson, Eagan, MN (US); Henry Louis Carbone, II, St. Paul, MN (US); Ryan Carroll, Phoenix, AZ (US); Ryan Jacob Urban, Mahtomedi, MN (US)

(73) Assignee: ECOLAB USA, INC., St. Paul, MN (US)

( * ) Notice: Subject to any disclaimer, the term of this patent is extended or adjusted under 35 U.S.C. 154(b) by 5 days.

(21) Appl. No.: 14/098,680

(22) Filed: Dec. 6, 2013

(65) Prior Publication Data
US 2014/0158709 A1 Jun. 12, 2014

Related U.S. Application Data

(60) Provisional application No. 61/734,532, filed on Dec. 7, 2012.

(51) Int. Cl.
| | | |
|---|---|---|
| *B01F 5/04* | (2006.01) | |
| *B67D 7/78* | (2010.01) | |
| *B01F 3/08* | (2006.01) | |

(52) U.S. Cl.
CPC ............ *B01F 5/0496* (2013.01); *B01F 3/0865* (2013.01); *B01F 5/0428* (2013.01); *B67D 7/78* (2013.01); *B01F 2003/0896* (2013.01)

(58) Field of Classification Search
USPC ............ 222/108, 110, 145.1, 488, 464.5, 72, 222/133, 318, 402.16, 455
See application file for complete search history.

(56) References Cited

U.S. PATENT DOCUMENTS

| | | | | |
|---|---|---|---|---|
| 2,171,687 | A | * | 9/1939 | De Lancey ................... 222/68 |
| 3,728,129 | A | * | 4/1973 | Sageant ..................... 426/569 |
| 3,863,843 | A | * | 2/1975 | Hechler, IV ................. 239/318 |
| 4,368,757 | A | * | 1/1983 | Finger ..................... 137/565.17 |
| 5,238,155 | A | * | 8/1993 | Blake, III .................... 222/190 |
| 5,443,094 | A | | 8/1995 | Olson et al. |
| 5,597,019 | A | | 1/1997 | Thomas et al. |
| 5,799,831 | A | * | 9/1998 | Spriggs et al. ............... 222/132 |
| 5,816,446 | A | * | 10/1998 | Steindorf et al. ............... 222/1 |

(Continued)

OTHER PUBLICATIONS

Ecolab USA Inc., PCT/US2013/073535 filed Dec. 6, 2013, "Notification of Transmittal of the International Search Report and the Written Opinion of the International Searching Authority, or Declaration" mailed Mar. 4, 2014.

*Primary Examiner* — Paul R Durand
*Assistant Examiner* — Vishal Pancholi
(74) *Attorney, Agent, or Firm* — McKee, Voorhees & Sease, PLC

(57) ABSTRACT

Methods, apparatuses, and systems for dispensing an off-gassing liquid product mixed with a diluting product are provided. A liquid product or product solution is moved through a primed product line and towards a dispenser. The liquid product is combined with the diluting product to create a solution. The solution is dispensed. The product line is cleared of unused or displaced liquid product by redirecting at least a portion of the unused or displaced liquid product in the product line to a displacement system operatively attached to the product line. The displacement system includes a check valve including a crack pressure that allows the unused or displaced product to be dispensed back into the product source or a separate, secondary container.

6 Claims, 12 Drawing Sheets

(56) References Cited

U.S. PATENT DOCUMENTS

| | | |
|---|---|---|
| 6,405,897 B1 * | 6/2002 | Jepson et al. ............... 222/108 |
| 6,679,437 B2 * | 1/2004 | Truelove ..................... 239/154 |
| 7,780,039 B2 * | 8/2010 | Criswell et al. ............. 222/108 |
| 2005/0084414 A1 | 4/2005 | Treiman |
| 2006/0243743 A1 * | 11/2006 | Mehus et al. ............... 222/133 |
| 2007/0059202 A1 | 3/2007 | Tichy et al. |
| 2009/0004068 A1 * | 1/2009 | Frisch ......................... 422/140 |
| 2009/0014474 A1 * | 1/2009 | Kennedy et al. ............ 222/372 |
| 2010/0133292 A1 | 6/2010 | Ware et al. |
| 2013/0206281 A1 | 8/2013 | Carroll |

* cited by examiner

SYSTEM FOR HANDLING DISPLACEMENT OF LIQUID PRODUCTS

CROSS REFERENCE TO RELATED APPLICATIONS

This application claims priority under 35 U.S.C. §119 to provisional application Ser. No. 61/734,532, filed Dec. 7, 2012, which is hereby incorporated by reference in its entirety.

FIELD OF THE INVENTION

The invention is directed towards liquid dispensers. More particularly, but not exclusively, the invention is directed towards liquid dispensers dispensing an off-gas producing liquid product that is combined with a diluting product.

BACKGROUND OF THE INVENTION

*Clostridium difficile* (C. diff) infection is a serious disease that takes a heavy toll on the people afflicted with it. The organism spores spread easily and are extremely difficult to kill. It has become such a problem that it is one of the leading hospital acquired infections in the United States. Reducing the spread of infection and addressing spores in the healthcare environment has become a focus area for hospitals, long term care facilities, other healthcare facilities, and other care centers.

Peroxides and peracids are two classes of chemicals known to effectively kill/inactivate microorganism spores, and these classes of chemistry are growing in acceptance for use in combating C. diff in the healthcare environment. In a concentrated form, these chemistries are generally quite harsh and often carry significant safety warning language and requirements for use of personal protective equipment (e.g., chemical resistant gloves, splash goggles, etc.). Despite the harshness of the concentrate and safety requirements, these chemistries offer substantial benefits of being able to be formulated for fast efficacy against C. diff spores and other bacteria and viruses, of having generally good material compatibility, of having good cleaning performance, and having little to no residue upon drying. Additionally, when properly diluted to levels intended for use in surface cleaning/disinfection, the diluted form may no longer be as hazardous as the concentrated form of the product and may no longer require use of the same level of personal protective equipment.

Concentrated dilute-on-site cleaning and disinfecting chemistries are preferred in the market as they offer sustainability benefits of reduced packaging and storage space requirements as compared to ready-to-use chemistries. On-site dilution is preferentially accomplished through a dispensing system that mixes the concentrated cleaning or disinfecting product with a second dilution product (e.g., water). Dispensing systems are preferred as they control the dilution rate and reduce the user's risk of exposure to the concentrated cleaning or disinfecting product. Dispensing systems generally pull the concentrated cleaning or disinfecting product from the product's package or container through some form of tube (product line) using a pump or venturi, blend it with the second dilution product, and dispense the product through an outlet where it can be put into a second container or directly used. In a conventional dispensing system, a foot valve, umbrella valve, or check valve is used on this product line to maintain prime in the product line. The liquid product in the product line is essentially contained between this foot/check valve and the outlet of the dispenser.

Peroxide and peracid chemistries decompose over time, resulting in gas formation (off-gassing). In a conventional dispensing system, this off-gassing can result in gas bubble formation on the inner wall of the product line tube that delivers the chemistry to the dispenser. The formation of these bubbles in the product line displaces concentrated liquid product and can cause concentrated product to be displaced through the outlet of the dispenser. This represents a safety concern for the end user as this type of concentrated chemistry has significant safety warnings and requires significant personal protective equipment (gloves, splash goggles, face shield, gown, possibly respirator) when in a concentrated form.

Therefore, there is a need in the art for methods, apparatuses, and/or systems to prevent or mitigate the displaced concentrated product displacing through a dispenser.

SUMMARY OF THE INVENTION

Therefore, it is a principal object, feature, and/or advantage of the present invention to provide an apparatus, method, and/or system that overcomes the deficiencies in the art.

It is another object, feature, and/or advantage of the present invention to provide a liquid dispenser that does not allow displaced, concentrated product to dispense from the dispenser.

It is another object, feature, and/or advantage of the present invention to provide a method of dispensing a liquid product using an unprimed product line.

It is yet another object, feature, and/or advantage of the present invention to provide a dispenser that is safe for an end user.

It is still a further object, feature, and/or advantage of the present invention to provide a system to capture any displaced liquid product in a product line.

These and/or other objects, features, and advantages of the present invention will be apparent to those skilled in the art. The present invention is not to be limited to or by these objects, features and advantages. No single embodiment need provide each and every object, feature, or advantage.

According to an aspect of the invention, a dispenser that is safe for the end user is provided. The dispenser can mitigate or completely solve the issue associated with dispensing a chemistry that off-gases and displaces concentrated liquid product. One solution is achieved through a dispenser design that enables the product line to drain back into the product container after each use to eliminate trapped product in the product line that can off-gas and displace concentrated chemistry. In the case of the concentrated peroxide and peracid products, the product containers generally use a venting method to then handle the off-gassing of the chemistry in the product bottle. According to another aspect of the invention, a dispenser that is safe for the end user is provided. The dispenser can mitigate or completely solve the issue of displacing liquid in a system that has naturally reacting chemistry that can cause off-gassing and displacement of concentrated liquid. The solution is achieved through different means of containing the displaced chemistry or allowing the displaced chemistry to be forced to a secondary container or back into the product container.

According to an aspect of the invention, a dispensing system for dispensing an off-gassing liquid product mixed with a diluting product is provided. The system includes a dispenser including a dispenser outlet, a product container containing the liquid product, a product line connecting the product container and dispenser, the product line including at least one check valve to maintain prime in the line, and a displacement system operatively attached to the product line and configured to redirect liquid product in the product line from displacing through the dispenser outlet.

The displacement system may include a displacement check valve. The displacement check valve can be included or separate than the priming check valve. The displacement valve includes a cracking pressure such that an amount of unused product in the product line will eventually be enough to "crack" the valve, which allows the product to drain back into a product source container or a separate, secondary container. This will prevent the unused product in the primed product line from being dispensed due to the off-gassing of the product.

According to another aspect of the invention, a method of dispensing an off-gassing liquid product from a product container is provided. The method includes moving the liquid product through a product line and towards a dispenser. The liquid product is combined with a diluting liquid product to create a solution, and the solution is dispensed. The product line is cleared of unused liquid product by redirecting at least a portion of the unused liquid product in the product line to a displacement system operatively attached to the product line.

According to yet another aspect of the invention, a dispenser is provided. The dispenser includes a product source, a product line operatively connected to the product source for transporting a portion of the first product from the product source, a mixing chamber operatively connected to the product line and configured to receive and mix a portion of the product with a second product, and a valve operatively connected to the product line between the product source and the mixing chamber. The valve maintains a prime in the product line. An unused portion of the first product is maintained in the product line after a combination of the first product and the second product are dispensed by the dispenser.

The methods, systems, and/or apparatuses of the invention can be used with generally any type of liquid product in generally any industry. For example, the invention may be used with a product that, in its concentrated form, may be hazardous to handle. The invention provides for a safeguard against accidental exposure of the concentrated substance, and aids in ensuring that only a diluted version of the liquid product is able to be dispensed. However, it should be appreciated that the invention can be used with generally any off-gassing or similar liquid, whether the liquid be hazardous or not. Furthermore, due to the flexibility of the invention, including nonspecific product lines and other attachments, the invention can be used in generally any industry in which a concentrated or otherwise potentially hazardous product is used such that the invention provides safeguards in the use of the product, no matter the type of industry.

DETAILED DESCRIPTION OF THE PREFERRED EMBODIMENTS

Figure 1:
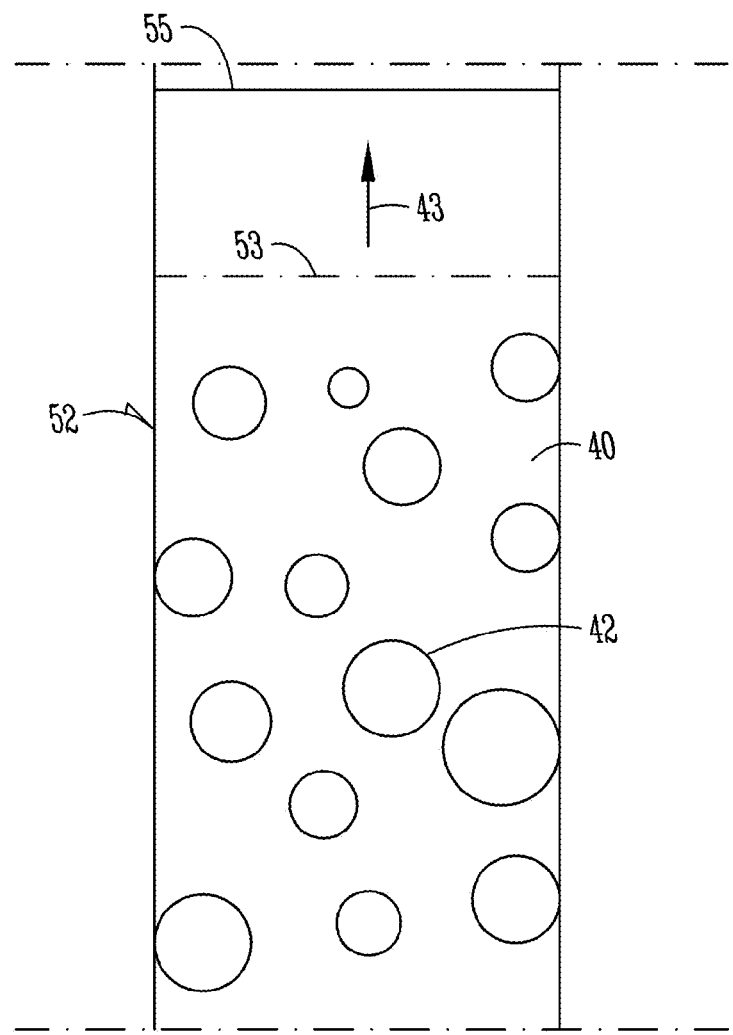
FIG. 1 is a schematic diagram of a product line containing a product chemistry that causes off-gassing in the product line.

FIG. 1 is a schematic diagram of a primed product line 52, or at least a section thereof. The primed product line 52 includes a liquid product 40, which comprises a chemistry that produces bubbles 42 caused by off-gassing. For example, the product might be a peroxyacetic acid/hydrogen peroxide chemistry, and the bubbles 42 or off-gassing occur due to the natural decomposition of the product. Other chemistries of liquid product may also cause similar reactions due to the natural degradation of the chemistry, which would also produce the bubbles 42 of the off-gassing. Thus, the invention is not to be limited to specific chemistries and/or products, and can be used with generally any type of product and in generally any industry. The off-gassing forms bubbles 42 that continue to build up on the wall of the product line 52. The failure of these bubbles 42 to propagate up and out of the line 52 causes the volume of the bubbles 42 to displace that same volume of product 40 upward and/or outward in the product line 52 towards the dispenser outlet 14. The displacement of the liquid product 40 out of the dispenser can create an unsafe condition, as the product 40 comprises a concentrated product that can be hazardous. As shown in FIG. 1, the product level could change from the level 53 up to and exceeding the level 55 in the direction of the arrow 43 due to the off-gassing of the chemistry of the liquid product 40.

Therefore, the present invention includes various solutions to account for the displacement of the liquid product 40, in both the product container 34 and an unprimed product line 38, as well as a primed product line 52.

Figure 2:
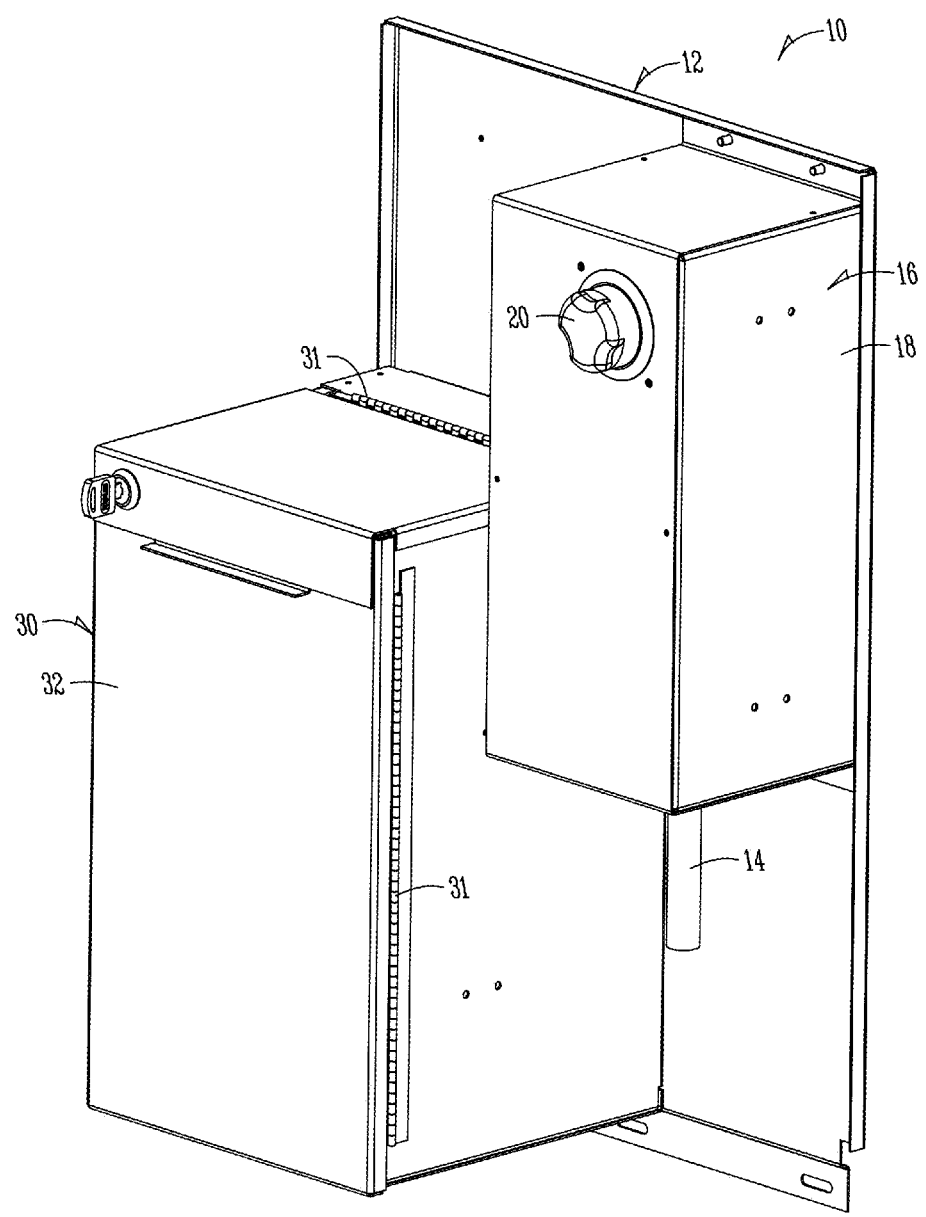
FIG. 2 is a perspective view of a dispenser system according to an embodiment of the present invention.

FIG. 2 is a perspective view of a dispensing system 10 according to an embodiment of the present invention. The dispensing system 10 includes a dispenser 12 having a dispenser outlet or head 14. The dispenser outlet 14 is configured to dispense a solution of combined concentrated liquid 40 and a diluting product 28 such that the solution comprises a desired or predetermined concentration of liquid product 40.

Figure 3:
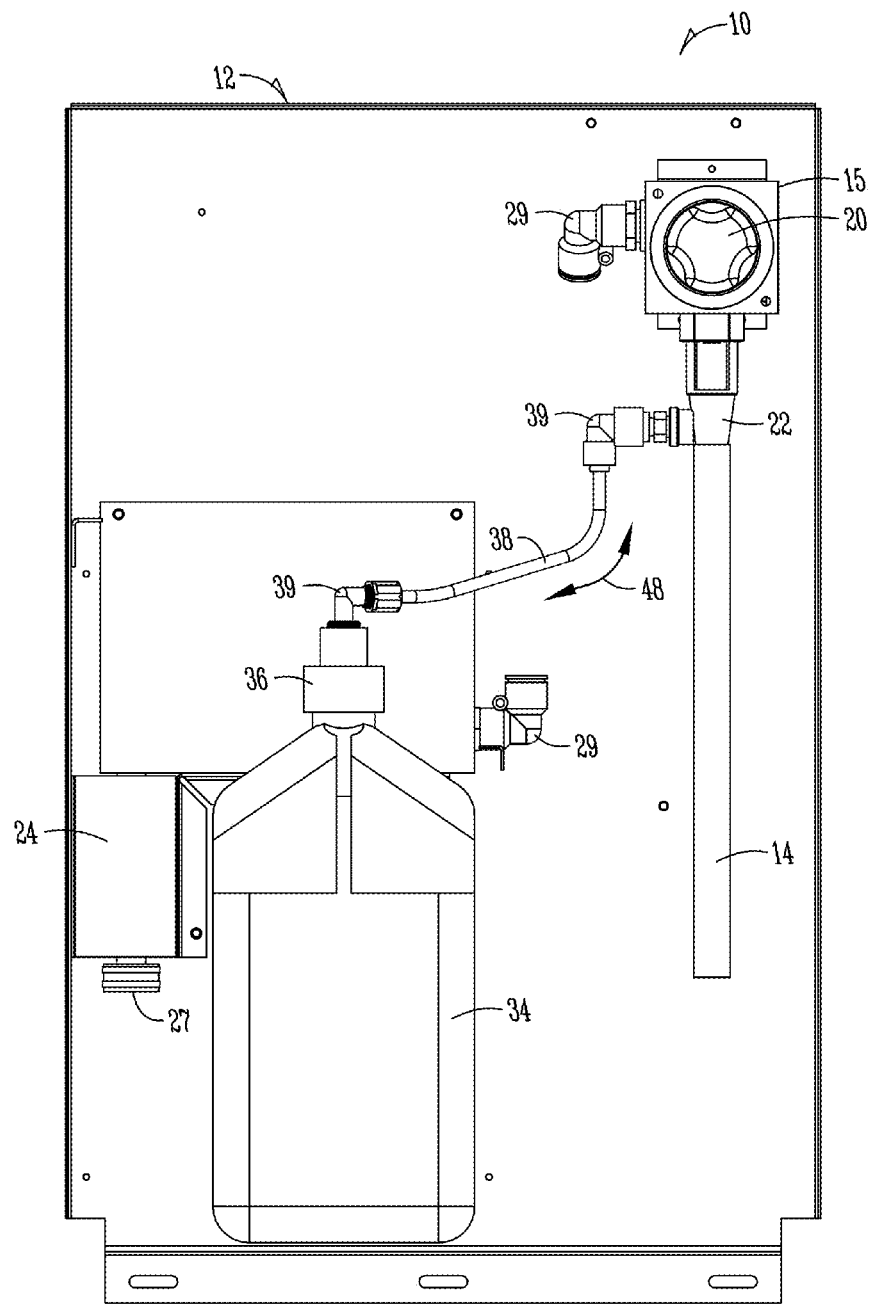
FIG. 3 is a front elevation view of some of the internal components of the dispenser of FIG. 2.
Figure 4:
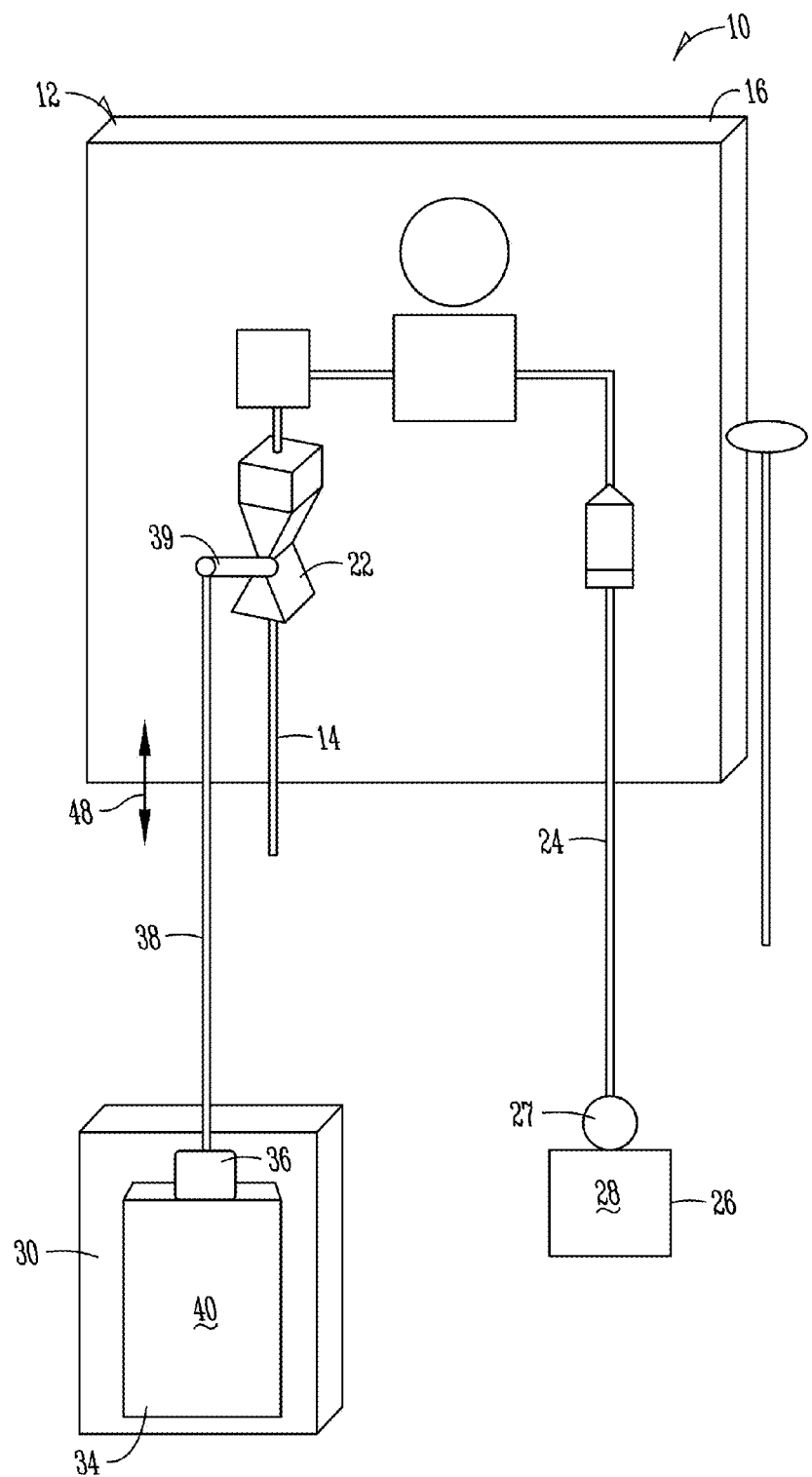
FIG. 4 is a schematic view of the dispenser of FIG. 2.

As shown in FIG. 2, the dispenser 12 includes a dispenser enclosure 16 comprising dispenser enclosure walls 18. FIGS. 3 and 4 show various components housed within the dispenser enclosure 16. For example, the dispenser outlet 14 may be positioned at least partially within the dispenser enclosure 16 and can extend therefrom. A mixing chamber 22, which may be an aspirator for combining the concentrated liquid product 40 and the diluting product 28, may also be partially housed within the dispenser enclosure 16. Other elements that are positioned at least partially within the dispenser enclosure 16 include a diluter elbow 29 for connecting a diluter line 24 to the mixing chamber 22, additional aspirators or pumps connected to the product line 38 and product container 34 for drawing the liquid product 40 to the mixing chamber 22, a product elbow connecter 39, and at least a portion of the unprimed product line 38. Other components may also be enclosed within the dispenser enclosure. In addition, not all the stated components need be fully or even partially enclosed within the dispenser enclosure 16, and the present invention contemplates other configurations for such a dispenser 12.

Also shown in FIGS. 2-4 is a product enclosure 30. The product enclosure 30 includes a plurality of enclosure walls 32, which may be hingeably connected to one another via hinges 31 to allow access to within the product enclosure 30. At least partially housed within the product enclosure 30 are a product container 34, container coupler 36, and at least a portion of a product line 38, which may include an elbow connecter 39 between the coupler 36 and line 38. As stated, the product container 34 will include a concentrated liquid product 40 that is to be combined with a diluting product 28, such as water, to create a solution having a desired concentration for cleaning or the like. The diluter source is connected to a diluting product valve 15, and can include a button 20 thereon to access the diluting product. The container coupler 36 is configured to connect the product container 34 to the product line 38 such that the product may be drawn from the container 34 and through the line 38 towards the mixing chamber 22 and dispenser head 14. It is noted that a feature of the invention includes the omission of any check valves, foot valves, umbrella valves, or any other one way valves at the product container coupler 36 or within the product line 38. Thus, the product line 38 may be considered an unprimed product line 38.

The unprimed product line 38 allows for handling of a displaced liquid product due to the bubbles 42 created by the off-gassing of the chemistry of the liquid product 40. As stated above, in normal product lines, the bubbles 42 will cause the liquid product in a primed product line to displace through the product line and potentially out of the dispenser head. In addition, these primed product lines include a one way valve, such as a check valve, to insure a prime or a storage of liquid product in the product line between dispensement of the solution through the dispenser 12. The configuration shown in FIGS. 2-4 mitigates or prevents the displacement by allowing any liquid product not dispensed during dispensement of the solution to drain back into the product container 34 or a secondary container. The draining is accomplished by the removal of one way valves in the product line 38, elbow connectors 39, container coupler 36, and/or container 34.

It is recognized that it is advantageous to have the product container 34 and the container coupler 36 seal when they are disconnected from each other to prevent any quantity of concentrated liquid product 40 from dripping or leaking from either the container 34 or coupler 36. Inclusion of valves in the container 34 and coupler 36 that are in a closed position when the container 34 and coupler 36 are disconnected and in an open position when container 34 and coupler 36 are connected is contemplated. Inclusion of such valves enables the product line 38 to be open and free of any blockages when the container 34 and coupler 36 are connected, allowing the concentrated liquid product 40 to drain completely from product line 38.

Therefore, the configuration shown in FIGS. 2-4 may be used in a following manner. The product container 34 containing a concentrated liquid product 40 is connected to an aspirator and mixing chamber 22 via a valveless and/or valveless and unprimed product line 38 connected to a container coupler 36. A diluting source 26, such as a water source, is connected to a diluting hookup 27, which includes a diluter or diluting line 24 between the diluter hookup 27 and the aspirator/mixing chamber 22. The connection may also include one or more diluter elbows 29 to direct the diluter line 24. When a solution (concentrated liquid product mixed with the diluting product) is to be used, a user activates the dispenser 12 to begin flow of the diluting product 28 and the concentrated liquid product 40. The products may be drawn via an aspirator or pump, such as that shown in FIGS. 3 and 4. The aspirator 22, including the size of the metering orifice connecting the product line 38 and aspirator, and/or size of the line 38 are configured such that the correct ratio of diluting product 28 to concentrated liquid product 40 is combined in the mixing chamber and dispensed via the dispensing outlet 14 as a concentrated solution. Once the desired volume of solution has been dispensed from the dispenser 12, the aspirator(s) is/are deactivated. Upon deactivation of the dispenser 12, any remaining liquid product 40 in the product line 38 is allowed to drain back into the product container 34 to clear the line 38 of any liquid product 40. The removal of liquid product 40 from the product line 38 may be accomplished via a pump, suction, or vacuum created on the product container 34, by force of gravity, or other means obvious to one skilled in the art. The removal of all liquid product 40 from the line 38 mitigates and/or prevents any displacement of liquid product 40 through the dispenser outlet 14 at an undesired time. Thus, the liquid product 40 is able to move fully through the product line 38 in both directions, as shown by the arrow 48 in FIGS. 3 and 4.

However, as the product line 38 will remain unprimed in between each dispensement of liquid product 40 and the solution, the dispensing system 10 must also be configured to account for any lag or delay in moving the liquid product 40 from the product container 34 and to the mixing chamber 22 to provide a desired concentration of solution for dispensing. Steps may be taken into account for this delay. For example, the size of the product line 38 and/or size of the metering orifice connected to the product line 38 may be varied to allow for more or less concentrated liquid product 40 to pass therethrough and to the mixing chamber 22. Furthermore, the dispenser 12 may be configured to have minimum times and amounts of solution dispensed therefrom during each dispensement to ensure that the end result of solution is a solution having a desired concentration or composition. Other variations can be added to the dispensing system 10 to ensure that the correct concentration of liquid product 40 to diluting product 28 is found in the dispensed solution.

In addition, it should be appreciated that the invention not be limited to a liquid, concentrated product mixing with a diluting product. It is also contemplated that a solid concentrated product be stored in the dispensing system and used to create a solution. In such a case, a liquid diluent can be mixed with the solid product to create a liquid product of a desired concentration. This can be stored at the location of the solid product, or in a separate container until it is to be used. The liquid product can then be further diluted with another liquid diluent, mixed with another liquid product, or used in its current form by the dispenser through an unprimed line. Once the use is complete, the combined product can then be drained back to a product container, which may be in the same location as the solid product or may be the separate product container. This allows the invention to be used with generally any type of product in which a liquid or semiliquid product is dispensed, and also allows the invention to be used in a larger variety of industries.

The foregoing configurations provide numerous benefits over existing dispensing systems. For example, the design is much simpler than existing systems, and includes fewer parts therein. Thus, fewer parts can break down or need replaced, increasing the likelihood that the dispensed solution will be at a proper concentration. In addition, the configurations shown and described allows for increased efficiency of the use of the liquid product 40 in the container 34. As the liquid product 40 will not be displaced through the product line 38 and out the outlet head 14, the configuration will allow the full amount of product in the container 34 to be used before having to be replaced. Furthermore, while there may be a delay in filling an unprimed product line 38 with product 40, the delay can be accounted for and easily overcome by including or adjusting the line size, minimum time of dispensing, minimum amount of dispensing, delayed pumping of diluting product 28, or the like. These changes may account for the delay in priming the line. However, the benefits of depriming or unpriming the product line 38 after each dispensement will overcome any such hurdles caused by the delay in pumping the product 40 through the product line for each dispensement.

Figure 5:
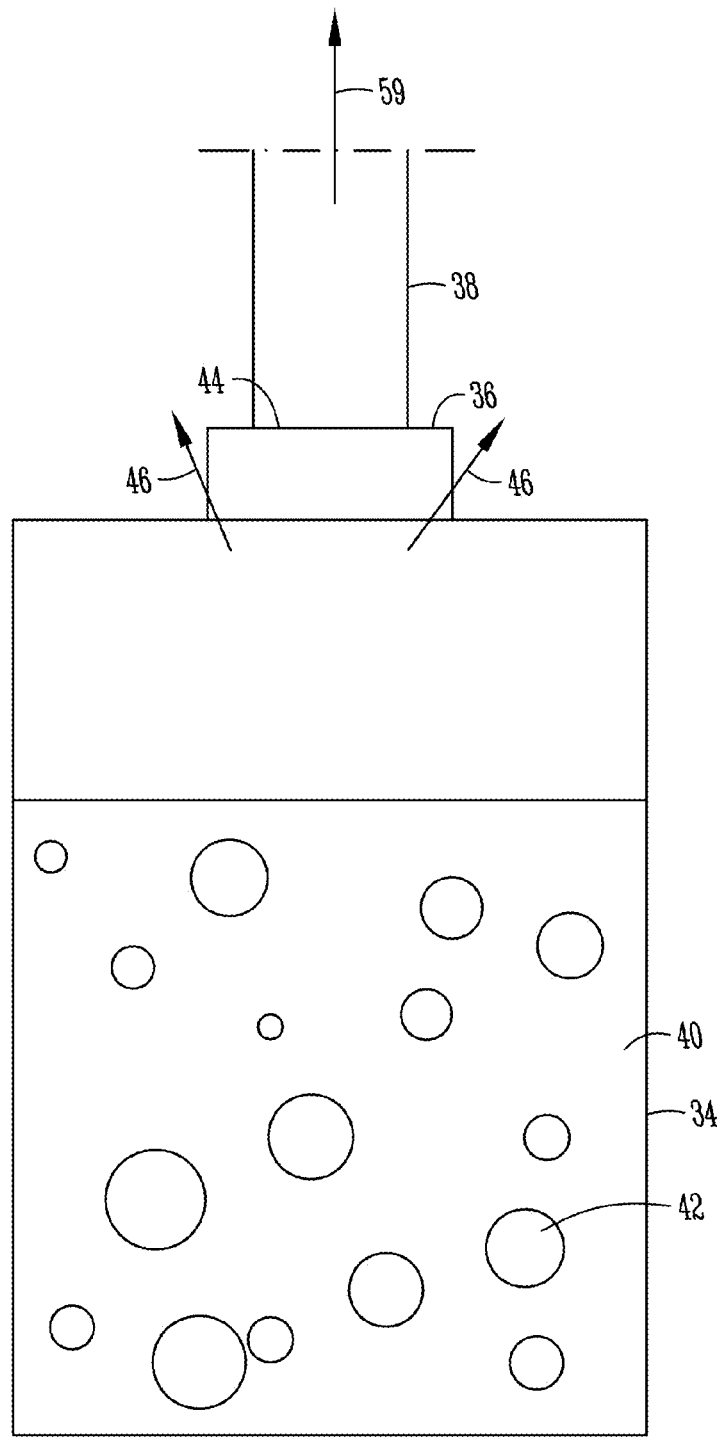
FIG. 5 is a schematic view of a dispenser system showing a vented product container.

FIG. 5 shows another embodiment of the dispensing system 10 as shown above. FIG. 5 is an enlarged view of a product container 34 connected to an unprimed product line 38 via a container coupler 36. As the unprimed line 38 will allow any unused liquid product 40 drained back into the product container, there may be more liquid product 40 stored in the container 34 at a time. This stored product 40 will continue to produce bubbles 42 formed by the off-gassing of the chemistry of the liquid product 40. These bubbles can create displacement and or pressure in container 34. Therefore, the embodiment shown in FIG. 5 includes the use of a vented fitment 44 included in the container coupler 36 between the product container 34 and the product line 38. The vented fitment may be any standard fitment as can be purchased in the art, and can be configured to be open and closed. For example, such a fitment may include a passage therethrough with an ePTFE membrane therein to allow gasses to pass through the passage, while not allowing the liquid to pass through. In addition, other liquid impermeable membranes may be used.

However, it should be appreciated that liquid permeable membranes may also be used such that some liquid is allowed to pass into the product line 38, while still allowing the gas from the bubbles 42 to escape outwardly from the product line and product containers 38, 34. As shown in FIG. 5, the vented fitment 44 may allow the gasses to pass as shown by the direction of the arrows 46. The arrow 59 shows the direction that the liquid product 40 may be pumped or otherwise moved towards the dispenser during dispensement of the solution.

While the vented fitment 44 is shown to be included with the container coupler 36, it should be appreciated that a vented fitment may be included generally anywhere on the container 34. For example, a vented fitment 44 including such a liquid impermeable membrane as discussed above may be included in one of the walls of the container. Thus, the fitment may be open to allow the gasses formed by the chemistry of the liquid product 42 to pass through, while ensuring that the liquid product itself will not pass through. This will also ensure that the passage from the container 34 to the product line 38 remains open and allows the liquid product 40 to pass through with ease. Other configurations which will be obvious to those skilled in the art are also contemplated to a part of the present invention.

Figure 6:
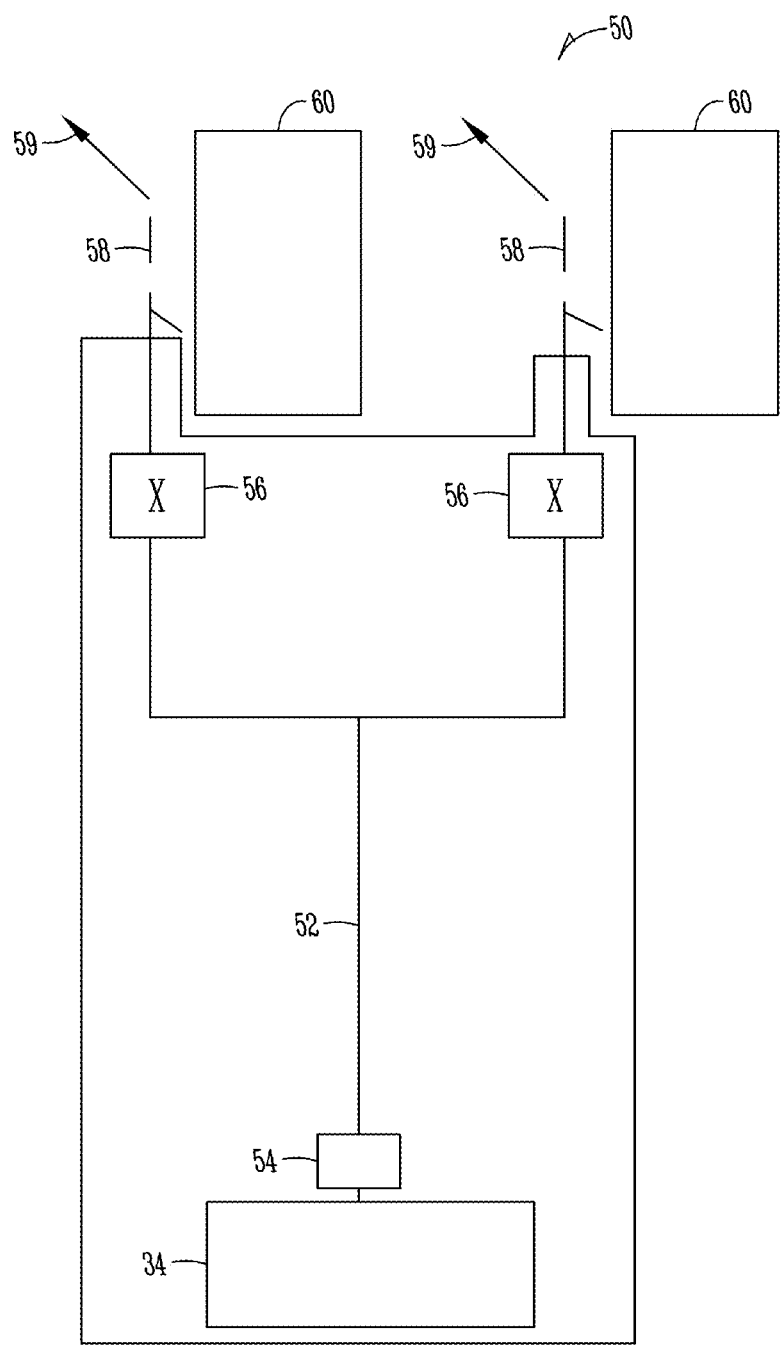
FIG. 6 is a schematic view of a dispensing system including a displacement system according to an embodiment of the present invention.

FIG. 6 is a schematic view of another dispensing system 50 according to the present invention and including a displacement system 60 connected to a product line 52. The dispensing system 50 shown in FIG. 6 includes a portion of the dispensing system as discussed in relation to FIGS. 1-4 above. As shown in FIG. 6, the dispensing system 50 includes a product container 34 connected to a product line 52 that is further connected to the mixing chamber 22 and other components of the dispenser as discussed above. However, in the configuration shown in FIG. 6, the product line 52 includes a check valve 54 or other one way valve positioned on the product line 52. Therefore, in the configuration shown in FIG. 6, the product line will remained primed, i.e., filled with a liquid product 40 in between dispensements of the solution through the dispenser head 14. For example, the check valve 54 may be an umbrella valve that allows the liquid product 40 to pass in a direction towards the dispenser, but does not allow the liquid product to drain back into the product container 34. Furthermore, additional check valves 56 may also be included on the product line to hold a product in the product line 52 to keep the product line 52 primed.

As such, the liquid 40 in the primed product line 52 may become displaced by the bubbles 42 created by the off-gassing chemistry of the liquid product 40. This displacement could cause the concentrated liquid product 42 to displace out of the dispenser head 14, which can cause an unsafe condition. Therefore, the configuration of the dispenser 50 shown in FIG. 6 includes the addition of one or more displacement systems 60 operatively connected to the primed product line 52. For example, the one or more displacement systems 60 may be connected to the product line 52 via a tee or wye fitting 58 positioned on the product line 52. As shown in FIG. 6, the fittings 58 will still allow product 40 be passed through and in the direction of the arrow 59 towards the dispenser 12. It should be further appreciated that, while FIG. 6 shows multiple displacement systems 60, and check valves 56, the present invention also includes the use of only one check valve 54 and displacement system 60.

The displacement system 60 may take many different forms, but is intended to mitigate or prevent any displacement of the liquid product 40 caused by the bubbles 42 formed due to the off-gassing chemistry of the liquid product 40. Therefore, the displacement system 60 may include a secondary container 64, or also may include a redirecting system to redirect any displaced liquid away from the dispenser head 14 until such time as the dispenser is activated to output a concentrated solution. It is further contemplated that the system may include both a secondary container 64 and a redirecting system as well. Thus, FIGS. 7-12 disclose various aspects of displacement systems 60 that may be used with the dispensing system 50 shown in FIG. 6. It is to be appreciated that FIGS. 7-12 are not an exhaustive list of potential displacement systems, and that the present invention contemplates that variations and changes obvious to the those skilled in the art are included as part of the present invention.

Figure 7:
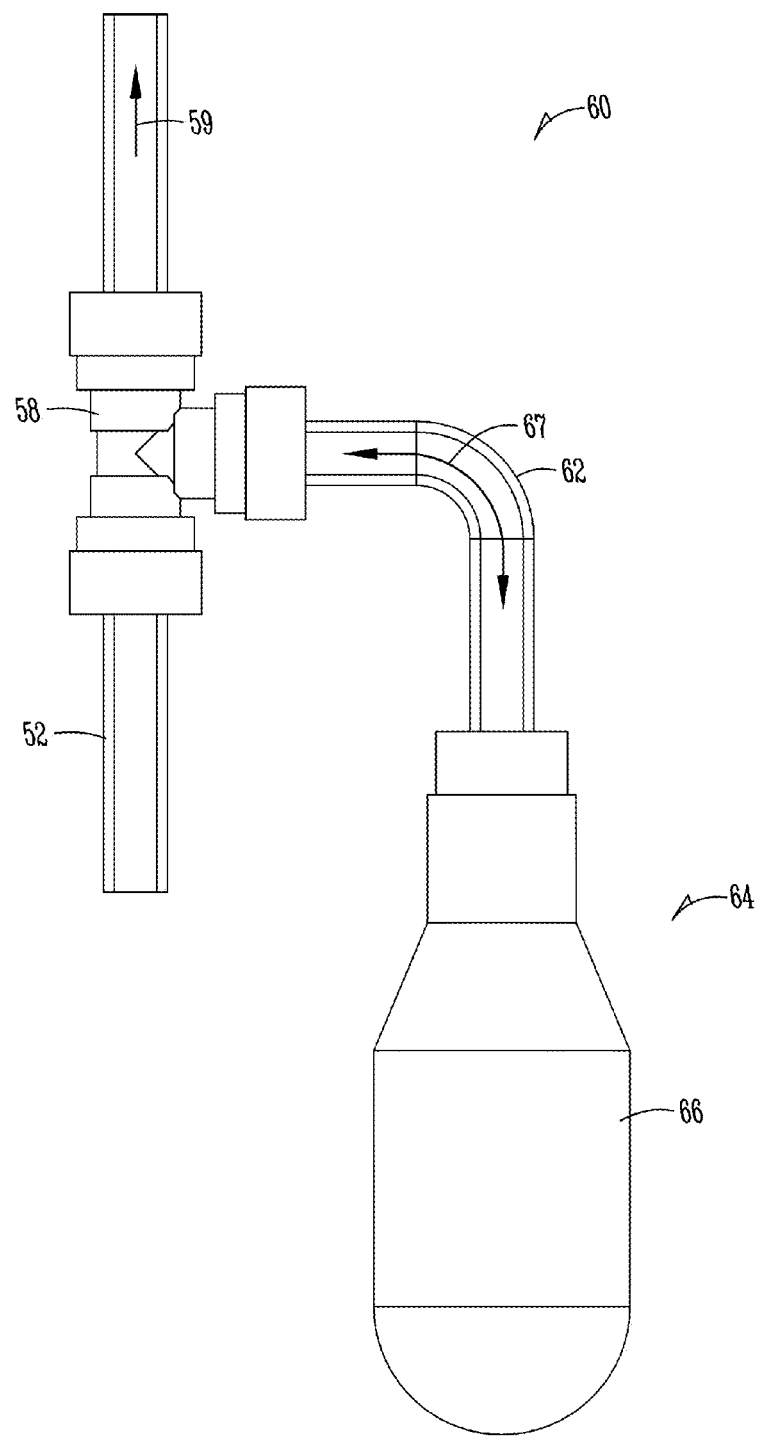
FIG. 7 is a view of an embodiment of a displacement system used with the dispensing system of FIG. 6 and including a bladder.

FIG. 7 shows a displacement system 60 including a secondary container 64 for accumulating any displaced liquid product 40 from the primed product line 52. Shown in FIG. 7, a tee fitting 58 is incorporated on the prime product line 52. A displacement tube 62 is connected to the tee fitting 58 and includes a bladder 66 attached to the opposite distal end thereof. Therefore, as the liquid product 40 in the primed product line 52 expands due to the bubbles 42 formed in the product line 52, any displaced product will be directed through the displacement tube 62 via tee fitting 58 and into the bladder 66. However, in the embodiment shown, the displacement tube 62 does not include a check valve or one way valve, such that the accumulated, displaced product in the bladder 66 may be evacuated upon the operation of the dispenser 12. For example, while the bladder 66 accumulates the displaced product, the aspirator and/or pump of the dispensing system 50 will work to draw the accumulated product from the bladder 66 to evacuate the bladder and combine the displaced liquid with the primed liquid in the product line 52 to move the product 40 in the direction as shown by the arrow 59 in FIG. 7 towards the dispenser. Thus, the displaced liquid product will be able to move in the directions shown by arrow 67 in the displacement tube 62. It is to be appreciated that the accumulated, displaced product in the bladder 66 may be the first used product upon dispensement, or the product in the bladder 66 may be allowed to accumulate until such time that the bladder fills such that the operation of the dispenser will naturally move the accumulated product from the bladder at the same rate as that taking from the product container 34. In addition, while the Figure shows a bladder 66 being used as a secondary container 64, the invention contemplates that other containers may be used, such that they are capable of storing the concentrated chemistry of the liquid product 40. The bladder may be made of a Teflon or kynar material such that the concentrated liquid product 40 will not erode or deteriorate the inside of the secondary container 64. However, other materials may be used as well.

Figure 8:
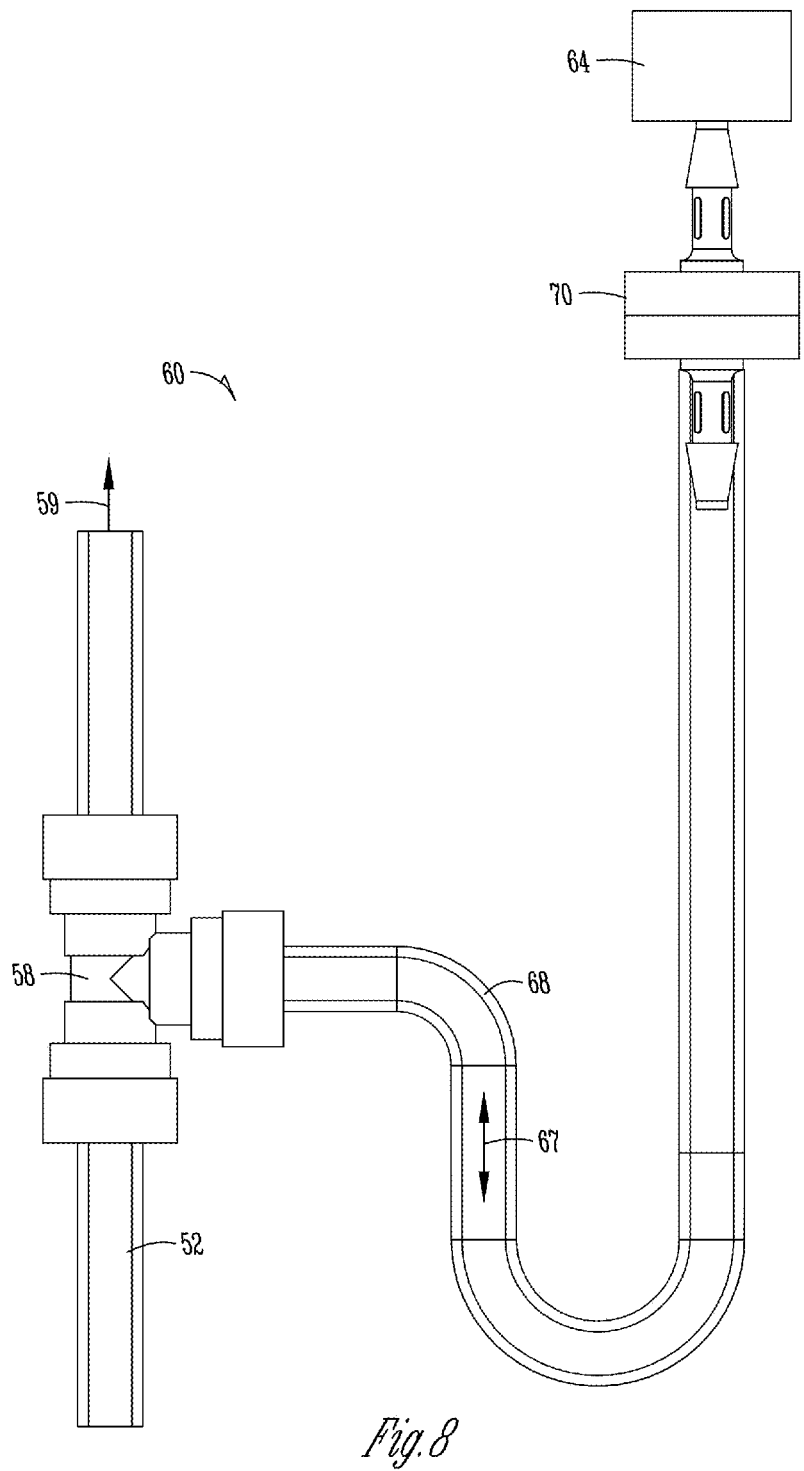
FIG. 8 is a view of another embodiment of a displacement system used with the dispensing system of FIG. 6 and including a "v-trap".

FIG. 8 shows another configuration of a displacement system 60 for use with the dispensing system 50 of FIG. 6. FIG. 8 shows a v-trap design including a v-trap tube 68 attached to a tee fitting 58 positioned on the primed product line 52. Any displaced liquid in the primed product line 52 enters the diverted v-trap tube 68 and continues to rise as more liquid enters in the v-trap. The v-trap tube 68 may be evacuated upon the next dispensement of the solution by the dispenser 12. Thus, the displaced product in the v-trap tube 68 may be moved in either direction, such as that shown by the direction of the arrow 67 in FIG. 8. Furthermore, a distal end of the v-trap tube 68 may include a v-trap check valve 70, which can be connected to a secondary container 64. The v-trap check valve 70 may allow movement in only one direction such that the secondary container 64 accumulates and traps any displaced liquid product 40. Once the secondary container 64 has been filled with an amount of displaced liquid product 40, the container can be removed from the line and disposed of accordingly. However, the v-trap check valve 70 may be configured such that the crack pressure of the valve 70 is such that the pressure may be overcome by the use of the pump or by the accumulation of the product in the container 64. It is to be appreciated that the check valve 70 may not be included in all configurations, and a secondary container 64 may be simply attached to the distal end of the v-trap tube 68. In addition, the secondary container 64 need not be included at all in this configuration. However, as mentioned, the displaced liquid may be evacuated upon dispensement at the dispenser head 14 of the solution to allow the displaced liquid to move in the direction shown by the arrow 59 in FIG. 8 towards the mixing chamber 22 and dispenser head 14.

Figure 9:
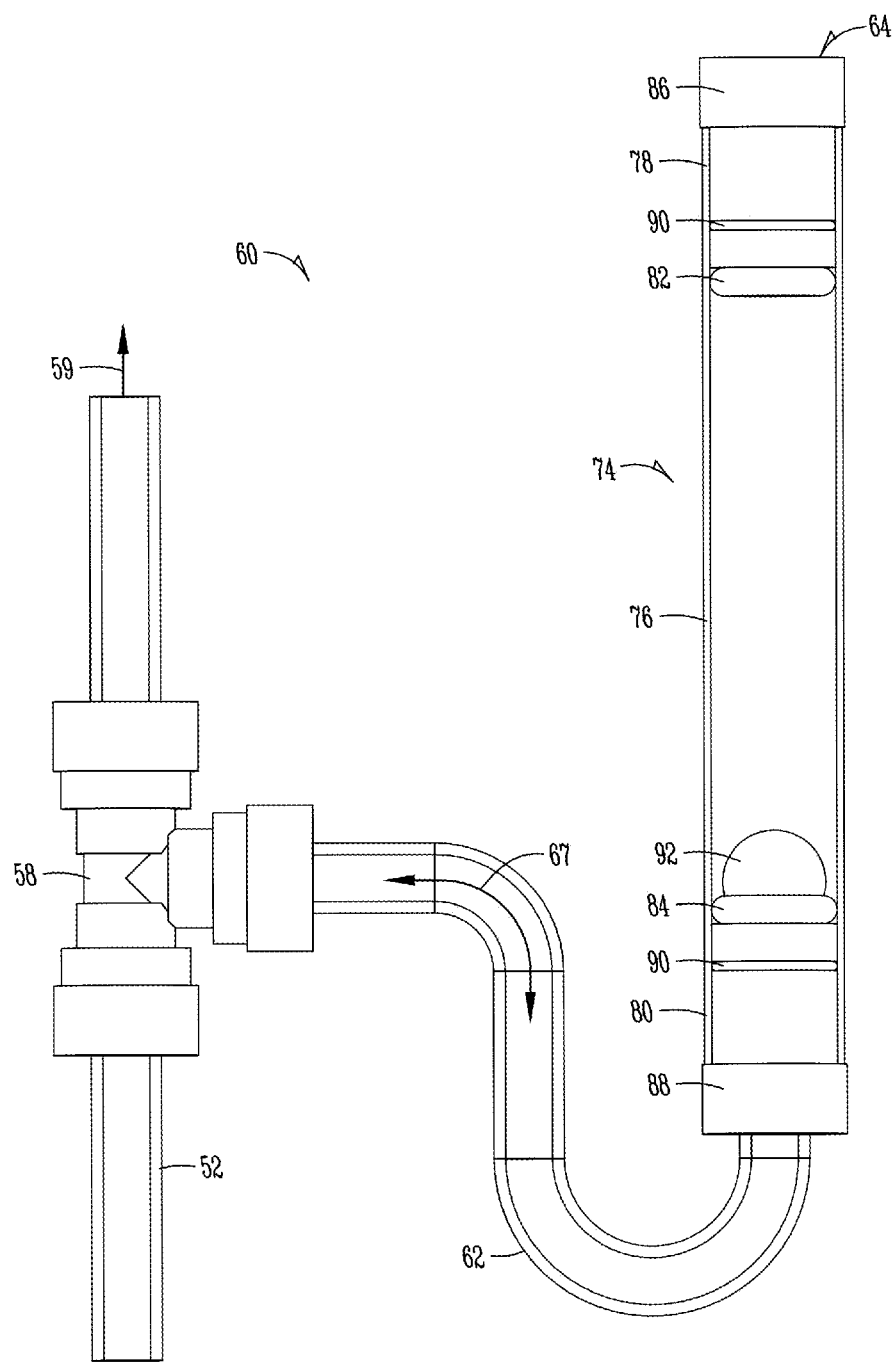
FIG. 9 is a view of another embodiment of a displacement system used with the dispensing system of FIG. 6 and including a canister with a floating ball.

FIG. 9 shows another configuration of a displacement system 60 for use with the dispensing system 50. As shown in FIG. 9, a displacement tube 62 is again attached to a tee fitting 58 positioned on the prime product line 52. At the distal end of the displacement tube 62 is positioned a tube or canister 74. The canister 74 is shown to be a cylinder 76 having a first end 78 and opposite second end 80. The first end 78 of the cylinder 76 includes a first insert 86 at the first end 78, while the second 80 includes a second insert 88 to be connected to the distal end of the displacement tube 62. The first and second inserts 86, 88 include apertures therethrough to not fully close the ends of the cylinder. Thus, the first insert 86 allows for air or atmospheric pressure to pass through, while the second insert 88 allows any displaced liquid to pass therethrough and into the interior of the canister 74. Positioned generally adjacent the inserts 86, 88 are first and second gaskets 82, 84. First and second gaskets 82, 84 are positioned at the first and second ends 78, 80 of the cylinder 76. The inserts may also include O-rings 90 to fluidly seal the inserts at the ends of the cylinder 76. Between the gaskets is positioned a ball 92, which may be considered a floating ball. It is noted that, while a ball 92 is shown and described between the first and second gaskets 82, 84, other objects may be used. For example, a disk or other object could be included between the gaskets and allowed to move therein such that the object will seal the canister when positioned adjacent the gasket.

The ball 92 rises as displaced liquid passes through the tee fitting 58, through the displacement tube 62, through the second insert 88, and into the cylinder 76. The ball 92 rises as the liquid enters and seals off at the first gasket 82 if the liquid level rises to that point. Thus, the ball 92 will block any liquid from passing beyond the first gasket 82 of the canister 74. The canister 74 is evacuated upon the next dispensement of the solution and the ball 92 seals off the second gasket 84 when the liquid level has been completely evacuated, allowing product 40 to be pulled from the primed pickup line 52. Thus, in the configuration shown in FIG. 9, the liquid stored in the secondary container 64, i.e., the canister 74, will be the first liquid product 40 used for combining with the diluting product 28 to create the solution being dispensed from the dispenser 12. It is to be appreciated that the accumulated, displaced product in the cylinder 76 may be the first used product upon dispensement, or the product in the cylinder 76 may be allowed to accumulate until such time that the cylinder fills such that the operation of the dispenser will naturally move the accumulated product from the cylinder at the same rate as that taking from the product container 34.

Figure 10:
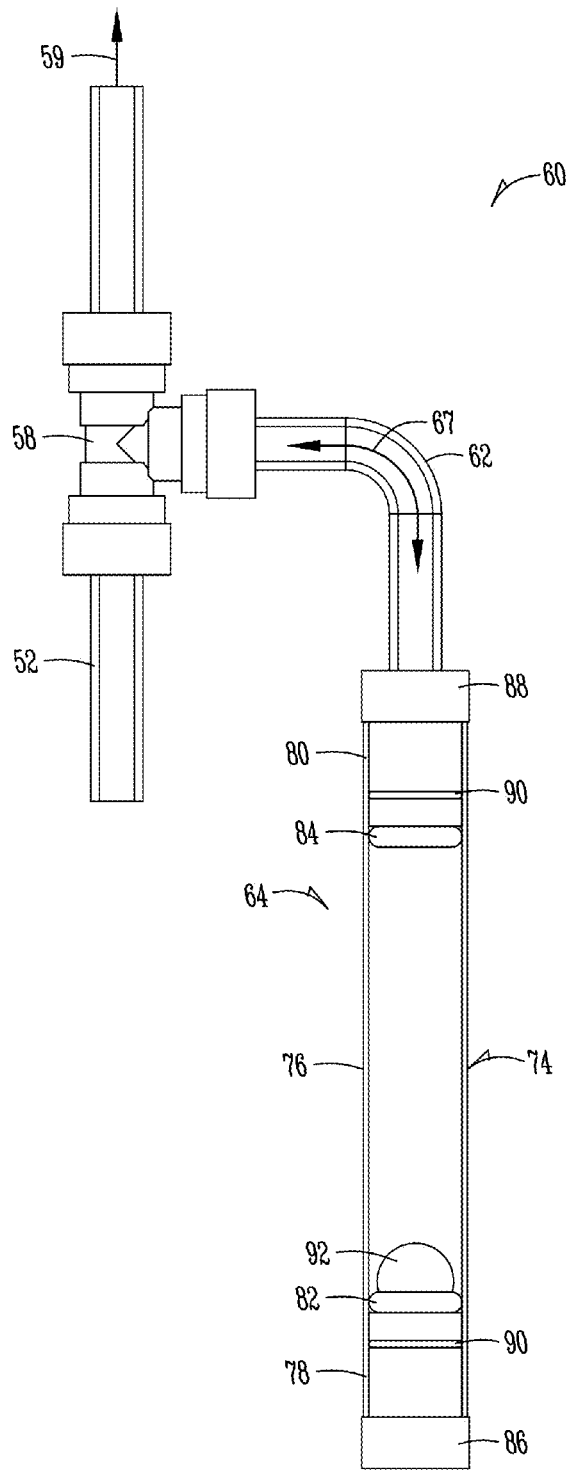
FIG. 10 is a view of another embodiment of a displacement system used with the dispensing system of FIG. 6 and including a canister with a non-floating ball.

FIG. 10 shows a displacement system 60 similar to that shown in FIG. 9. For example, FIG. 10 also includes the canister 74 including the gaskets 82, 84 and ball 92. However, in the configuration shown in FIG. 10, the ball 92 will seal off the first gasket 82 when the dispenser 12 is not in use, allowing the product 40 to be displaced into the interior of the cylinder 76 of the canister 74. When the dispenser 12 is activated 12, the liquid product 40 is evacuated as the ball 92 rises to seal the second gasket 84, thus allowing additional product 40 to be pulled from the primed pickup line 52.

Figure 11:
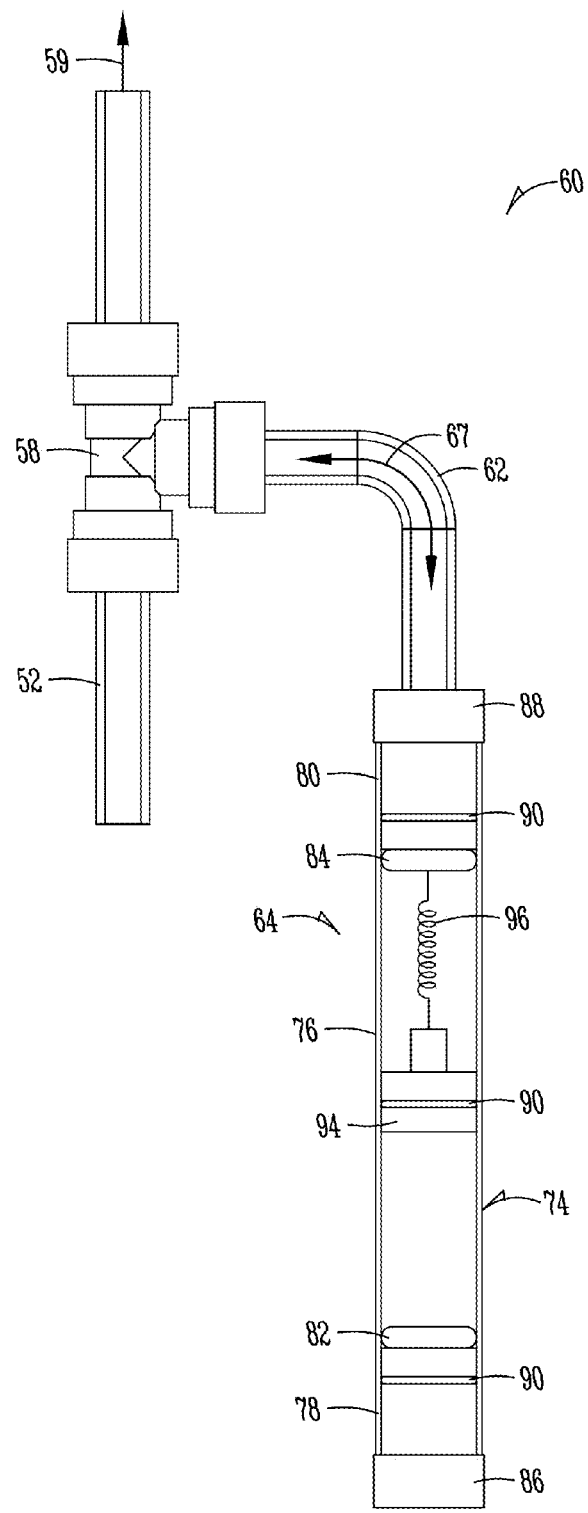
FIG. 11 is a view of another embodiment of a displacement system used with the dispensing system of FIG. 6 and including a canister with a spring-loaded disk.

FIG. 11 discloses yet another aspect of the present invention including a displacement system 60 including a secondary container 64. The secondary container 64 of FIG. 11 includes a canister 74 comprising a cylinder 76 having first and second ends 78, 80. First and second inserts 86, 88 are included at the first and second ends 78, 80 to seal the ends of the cylinder, while allowing liquid to pass through the second insert 88. In addition, first and second gaskets 82, 84 are positioned adjacent the first and second inserts 86, 88. However, in the configuration shown in FIG. 11, a disk 94 is attached to a spring 96 connected at the second end 80 of the cylinder 76. When the dispenser 12 is not activated, the spring 96 forces the disk 94 downwards towards the first end 78 of the cylinder 76, which allows the canister 74 to fill with any displaced liquid product 40. When the dispenser 12 is activated, the liquid in the canister is evacuated as the disk 94 is pulled towards the second gasket 84, thus sealing the canister 74 and allowing for liquid product 40 to be pulled from the primed product line 52 once the canister has been fully evacuated. As shown, the disk 94 may include an O-ring 90 to aid in fluidly sealing the disk within the cylinder 76.

In addition, it should be contemplated that the orientation of the canister may be reversed such that the canister extends generally upward to reverse the flow of the liquid through the canister and towards the dispenser in the direction of the arrow 59 in FIG. 11. Furthermore, the orientation and configuration of the spring 96 can be varied as well. For example, the spring can be either a compression spring or an extension spring such that the accumulated product moves the disk 94 away from second gasket 84, instead of the spring 96 maintaining the disk 94 away from the second gasket 84. As such, the invention also contemplates that the canister need not be vertical, and can be horizontal or generally any angle. Thus, while FIG. 11 shows the canister in a generally vertical manner, it should be appreciated that the present invention contemplates that the canister may be rotated at any direction with respect to both the vertical and horizontal plane. Furthermore, while a disk is shown as the object connected to the spring between the gaskets, other objects, such as balls or the like, may also be used to create the seal.

Figure 12:
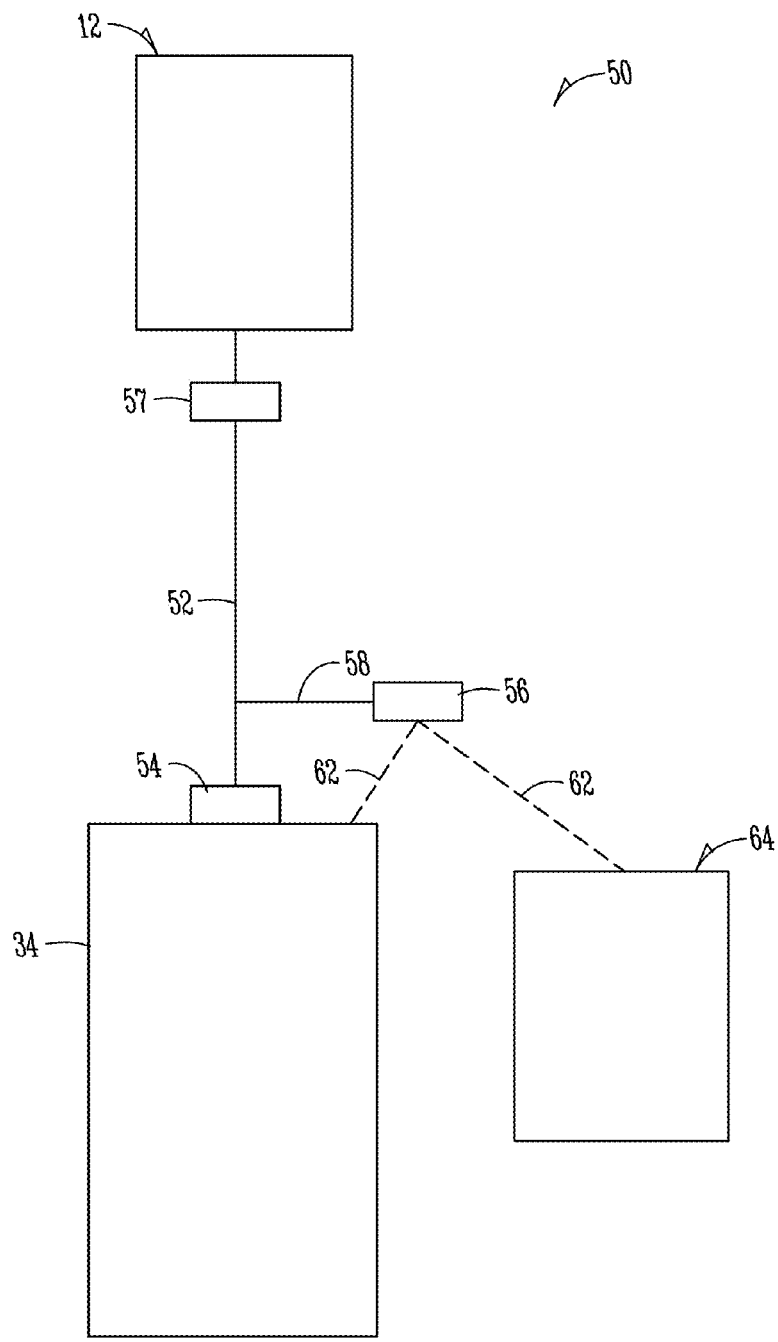
FIG. 12 is a view of another embodiment of a displacement system used with the dispensing system of FIG. 6 and including an additional check valve incorporated with the product line.

FIG. 12 shows another configuration of the dispensing system 50. As shown in FIG. 12, a product container 34 is connected to a dispenser 12 via a primed product line 52 having a check valve 54 positioned on the product line 52 to maintain prime in the line between dispensements of the solution. A second valve 56 is positioned either at an upper portion of the product line 52 or offset from the product line and connected via fitting 58. The second or additional check valve 56 allows the off-gassing chemistry of the product to create pressure and displace the product through the check valve, and into either a second container 64 or back into the product container 34 via a displacement tube 62. This may be accomplished by having the additional or second check valve 56 to have a lower crack pressure than the upper check valve 57. This allows the pressure and displacement to be removed from the product line 52 and displaced into the secondary container 64 or to be directed back into the original product container 34. The configuration could also be accomplished with a single fitting 54 attached to the product container 34 with the upward facing check valve and downward facing check valve in a single fitting, and with the directional check valves having different crack pressures to allow the product to drain back into the product container 34 only when the pressure reached a certain level in the product line 52.

The invention has been shown and described above and includes many other variations not explicitly discussed or disclosed. In addition, the materials of the components may be varied according to the chemistry of the product being combined with the diluting product to create the solution. For example, the product lines and tubes may comprise of Teflon, kynar, PVC, PE, HDPE, polyvinylidene difluoride (PVDF), or other material. In addition, the sizes, locations, orientations, and the like of the containers, dispenser, product lines, and other connections may be varied as well according to the type of product used and the desired output for the product.

The foregoing description has been presented for purposes of illustration and description, and is not intended to be an exhaustive list or to limit the invention to the precise forms disclosed. It is contemplated that other alternative processes obvious to those skilled in the art are to be considered to be included in the invention.

What is claimed is:

1. A dispensing system for dispensing an off-gassing liquid product mixed with a diluting product, comprising:
    a dispenser including a dispenser outlet;
    a product container containing the liquid product;
    a product line connecting the product container and dispenser, the product line including at least one check valve to maintain prime in the line; and
    a passive displacement system operatively attached to the product line and configured to redirect liquid product in the product line from displacing through the dispenser outlet, said displacement system comprising a displacement check valve operatively connected to the product line;
    wherein the displacement check valve has a lower crack pressure than the at least one check valve of the product line to allow the liquid product to drain from the product line to at least the product container to prevent displacement of the liquid product; and
    said passive displacement system utilizing the expansion of the off-gassing liquid product only to break the crack pressure of the displacement check valve;
    wherein the displacement check valve and the at least one check valve maintaining prime in the line are contained in a single fitting.

2. The dispensing system of claim 1 wherein the liquid product drains to a secondary container.

3. The dispensing system of claim 1 wherein the product line comprises polyvinylidene difluoride (PVDF).

4. The dispensing system of claim 1 further comprising a venting fitment operatively connected to the product container to vent gas and/or pressure produced by the liquid product.

5. A dispenser, comprising:
    a product source;
    a product line operatively connected to the product source for transporting a portion of the first product from the product source;
    a mixing chamber operatively connected to the product line and configured to receive and mix a portion of the product with a second product; and
    a valve operatively connected to the product line between the product source and the mixing chamber;
    a displacement check valve between the valve and the product source, said displacement check valve has a lower crack pressure than the valve of the product line to allow the liquid product to drain from the product line to prevent displacement of the liquid product;
    said displacement check valve configured to direct at least some of the liquid product to drain back into the product source;
    wherein the valve maintains a prime in the product line; and
    wherein an unused portion of the first product is maintained in the product line after a combination of the first product and the second product are dispensed by the dispenser;
    wherein the displacement check valve and the valve maintaining prime in the line are contained in a single fitting.

6. The dispenser of claim 5 wherein the first product is a liquid product and the second product is water.

* * * * *